(12) United States Patent
Franklin et al.

(10) Patent No.: US 11,684,719 B2
(45) Date of Patent: Jun. 27, 2023

(54) METHODS OF TREATMENT USING A SYRINGE EXTRUSION ACCESSORY

(71) Applicant: Allergan, Inc., Irvine, CA (US)

(72) Inventors: Ethan W. Franklin, Santa Barbara, CA (US); Justin J. Schwab, San Francisco, CA (US)

(73) Assignee: Allergan, Inc., Irvine, CA (US)

( * ) Notice: Subject to any disclaimer, the term of this patent is extended or adjusted under 35 U.S.C. 154(b) by 381 days.

(21) Appl. No.: 16/510,808

(22) Filed: Jul. 12, 2019

(65) Prior Publication Data
US 2019/0351146 A1 Nov. 21, 2019

Related U.S. Application Data

(63) Continuation of application No. 15/011,897, filed on Feb. 1, 2016, now Pat. No. 10,357,615, which is a
(Continued)

(51) Int. Cl.
*A61M 5/31* (2006.01)
*A61M 5/315* (2006.01)
*A61M 5/50* (2006.01)

(52) U.S. Cl.
CPC ...... *A61M 5/3137* (2013.01); *A61M 5/31555* (2013.01); *A61M 5/31556* (2013.01);
(Continued)

(58) Field of Classification Search
CPC .......... A61M 5/31556; A61M 5/31568; A61M 5/31576; A61M 5/3158; A61M 5/31581;
(Continued)

(56) References Cited

U.S. PATENT DOCUMENTS 977,282 A * 11/1910 De Vilbiss ............ E04F 21/165
222/391
1,250,114 A 12/1917 Bigelow et al.
(Continued)

FOREIGN PATENT DOCUMENTS

CN 2088857 11/1991
CN 2088857 U 11/1991
(Continued)

OTHER PUBLICATIONS

Bleyer, "SIS Facial Implant 510(k) Summary," Cook Biotech Inc., May 2005, 1 page.
(Continued)

*Primary Examiner* — James D Ponton
(74) *Attorney, Agent, or Firm* — Mintz Levin Cohn Ferris Glovsky and Popeo, P.C.

(57) ABSTRACT

A method of treatment may include providing a syringe having medicinal fluid therein for administering to a patient and coupling an attachment portion of an extrusion accessory having a handle and a pawl to a flange portion of the syringe. The pawl may have first and second ends, and be hingedly and rotatably coupled relative to the handle at a first position at the first end and at a second position between the first and second ends. The method may further include applying a force to translate the handle in a direction substantially perpendicular relative to a longitudinal axis of the syringe to cause axial movement of the second end of the pawl. The second end of the pawl may be engaged with a
(Continued)

plunger of the syringe and axial movement of the second end of the pawl may drive the plunger forward to extrude the medicinal fluid from the syringe.

20 Claims, 2 Drawing Sheets

Related U.S. Application Data continuation of application No. 14/284,285, filed on May 21, 2014, now abandoned.

(60) Provisional application No. 61/826,878, filed on May 23, 2013.

(52) U.S. Cl.
CPC ...... *A61M 5/31581* (2013.01); *A61M 5/5013* (2013.01); *A61M 2005/3139* (2013.01)

(58) Field of Classification Search
CPC ............ A61M 5/3137; A61M 5/31526; A61M 5/31555; A61M 5/5013; A61M 2005/3139
See application file for complete search history.

(56) References Cited

U.S. PATENT DOCUMENTS

| | | |
|---|---|---|
| 1,558,037 A | 10/1925 | Morton |
| 1,591,021 A | 7/1926 | Davis |
| 2,007,140 A | 7/1935 | Ragnar |
| 2,302,986 A | 11/1942 | Vollrath |
| 2,491,978 A | 12/1949 | Helfman |
| 2,551,902 A | 5/1951 | Rieck |
| 2,737,946 A * | 3/1956 | Hein, Jr. ............... A61M 5/30 604/70 |
| 2,853,070 A | 9/1958 | Julliard |
| 3,086,530 A | 4/1963 | Groom |
| 3,161,323 A | 12/1964 | Bent |
| D202,754 S | 11/1965 | Fnftolin |
| D214,112 S | 5/1969 | Langdon |
| 3,517,668 A * | 6/1970 | Brickson ............... A61D 7/00 604/209 |
| 3,595,231 A | 7/1971 | Pistor |
| D224,066 S | 6/1972 | McDonald |
| 3,720,211 A | 3/1973 | Kyrias |
| 3,767,085 A | 10/1973 | Cannon et al. |
| 3,807,048 A | 4/1974 | Malmin |
| 3,910,282 A | 10/1975 | Messer et al. |
| 3,916,777 A | 11/1975 | Earl |
| 3,977,574 A * | 8/1976 | Thomas ............... B01L 3/0279 604/209 |
| 4,064,879 A | 12/1977 | Leibinsohn |
| 4,240,423 A | 12/1980 | Akhavi |
| 4,240,426 A | 12/1980 | Akhavi |
| 4,273,122 A | 6/1981 | Whitney et al. |
| 4,326,517 A | 4/1982 | Whitney et al. |
| 4,346,708 A | 8/1982 | Leeven |
| 4,444,560 A | 4/1984 | Jacklich |
| 4,529,401 A | 7/1985 | Leslie et al. |
| 4,581,022 A * | 4/1986 | Leonard ............ A61M 5/31581 222/391 |
| 4,617,016 A | 10/1986 | Blomberg |
| 4,624,659 A | 11/1986 | Goldberg |
| 4,671,255 A | 6/1987 | Dubrul et al. |
| 4,693,684 A * | 9/1987 | Blatherwick ............ A61C 5/62 433/90 |
| 4,695,273 A | 9/1987 | Brown |
| 4,699,612 A | 10/1987 | Hamacher |
| 4,710,172 A * | 12/1987 | Jacklich ............... A61M 5/486 604/209 |
| 4,710,178 A * | 12/1987 | Henri ............... A61M 5/31581 604/209 |
| 4,719,918 A | 1/1988 | Bonomo et al. |
| 4,755,169 A | 7/1988 | Sarnoff |
| 4,759,750 A | 7/1988 | Devries |
| 4,779,770 A | 10/1988 | Herold |
| 4,800,901 A | 1/1989 | Rosenberg |
| 4,832,692 A | 5/1989 | Box |
| 4,841,948 A | 6/1989 | Bauser et al. |
| 4,841,992 A | 6/1989 | Sasaki et al. |
| 4,846,886 A | 7/1989 | Fey et al. |
| D303,010 S | 8/1989 | Jabbusch |
| 4,869,717 A | 9/1989 | Adair |
| 4,908,029 A | 3/1990 | Bark et al. |
| 4,955,905 A | 9/1990 | Reed |
| 4,957,744 A | 9/1990 | dellaValle et al. |
| 5,019,053 A * | 5/1991 | Hoffman ............... A61M 5/28 604/220 |
| 5,024,656 A | 6/1991 | Gasaway et al. |
| 5,046,506 A | 9/1991 | Singer |
| 5,066,303 A | 11/1991 | Bark et al. |
| 5,092,348 A | 3/1992 | Dubrul et al. |
| 5,100,390 A | 3/1992 | Lubeck et al. |
| 5,104,375 A | 3/1992 | Lubeck et al. |
| 5,116,358 A | 5/1992 | Granger et al. |
| 5,127,436 A | 7/1992 | Campion et al. |
| 5,141,496 A | 8/1992 | Dalto et al. |
| 5,211,644 A | 5/1993 | VanBeek et al. |
| 5,258,013 A | 11/1993 | Granger et al. |
| 5,270,685 A | 12/1993 | Hagen |
| 5,279,544 A | 1/1994 | Gross |
| 5,295,980 A | 3/1994 | Ersek |
| 5,305,788 A | 4/1994 | Mayeux |
| 5,318,544 A | 6/1994 | Drypen |
| 5,322,511 A | 6/1994 | Armbruster et al. |
| 5,344,407 A | 9/1994 | Ryan |
| 5,354,279 A | 10/1994 | Hofling |
| 5,368,572 A | 11/1994 | Shirota |
| 5,383,851 A | 1/1995 | Mackinnon, Jr. |
| 5,405,330 A | 4/1995 | Zunitch et al. |
| 5,433,352 A | 7/1995 | Ronvig |
| 5,478,327 A | 12/1995 | McGregor et al. |
| 5,540,657 A | 7/1996 | Kurjan |
| 5,549,672 A | 8/1996 | Maddock et al. |
| 5,611,809 A | 3/1997 | Marshall et al. |
| D378,939 S | 4/1997 | Smith et al. |
| 5,690,618 A | 11/1997 | Smith et al. |
| 5,752,970 A | 5/1998 | Yoon |
| 5,807,340 A | 9/1998 | Pokras |
| 5,817,033 A | 10/1998 | DeSantis |
| 5,823,998 A * | 10/1998 | Yamagata ............ A61M 5/2448 604/131 |
| 5,824,335 A | 10/1998 | Dorigatti et al. |
| 5,846,225 A | 12/1998 | Rosengart et al. |
| 5,891,106 A * | 4/1999 | Butuzov ............... A61M 5/24 604/209 |
| 5,941,845 A | 8/1999 | Tu et al. |
| 5,964,737 A | 10/1999 | Caizza |
| D424,194 S | 5/2000 | Holdaway et al. |
| 6,077,251 A | 6/2000 | Ting et al. |
| 6,102,929 A | 8/2000 | Conway et al. |
| 6,159,233 A | 12/2000 | Matsuzawa |
| 6,171,276 B1 | 1/2001 | Lippe |
| 6,183,434 B1 | 2/2001 | Eppstein |
| D441,077 S | 4/2001 | Garito et al. |
| 6,231,552 B1 | 5/2001 | Jentzen |
| 6,231,570 B1 | 5/2001 | Tu et al. |
| 6,283,951 B1 | 9/2001 | Flaherty et al. |
| 6,293,925 B1 | 9/2001 | Safabash et al. |
| 6,303,518 B1 | 10/2001 | Aceti |
| 6,312,412 B1 | 11/2001 | Saied |
| 6,432,046 B1 | 8/2002 | Yarush et al. |
| 6,451,240 B1 | 9/2002 | Sherman et al. |
| 6,482,187 B1 | 11/2002 | Gibbs |
| 6,488,651 B1 | 12/2002 | Morris |
| 6,551,290 B1 | 4/2003 | Elsberry et al. |
| 6,595,960 B2 | 7/2003 | West et al. |
| 6,607,512 B2 | 8/2003 | Oliver |
| 6,607,513 B1 | 8/2003 | Down |
| 6,611,707 B1 | 8/2003 | Prausnitz et al. |
| 6,613,010 B2 | 9/2003 | Castellano |
| 6,616,448 B2 | 9/2003 | Friedman |

(56) References Cited

U.S. PATENT DOCUMENTS

| | | |
|---|---|---|
| D483,116 S | 12/2003 | Castellano |
| 6,689,095 B1 | 2/2004 | Garitano et al. |
| 6,689,103 B1 | 2/2004 | Palasis |
| 6,780,171 B2 | 8/2004 | Gabel |
| 6,783,514 B2 | 8/2004 | Tovey et al. |
| 6,824,526 B2 | 11/2004 | Castellano |
| 6,896,666 B2 | 5/2005 | Kochamba |
| 6,901,850 B2 | 6/2005 | Corominas |
| 6,908,453 B2 | 6/2005 | Fleming |
| 6,936,297 B2 | 8/2005 | Roby et al. |
| 6,945,952 B2 | 9/2005 | Kwon |
| 7,004,928 B2 | 2/2006 | Aceti |
| 7,018,356 B2 | 3/2006 | Wise et al. |
| 7,033,337 B2 | 4/2006 | Hjertman |
| 7,041,088 B2 | 5/2006 | Nawrocki et al. |
| 7,047,070 B2 | 5/2006 | Wilkinson et al. |
| 7,048,729 B2 | 5/2006 | Meglin et al. |
| 7,097,631 B2 | 8/2006 | Trautman |
| 7,108,681 B2 | 9/2006 | Gartstein |
| 7,115,108 B2 | 10/2006 | Wilkinson et al. |
| 7,150,726 B2 | 12/2006 | Dalton |
| 7,302,885 B2 | 12/2007 | Townsend |
| 7,361,163 B2 | 4/2008 | Cohen |
| 7,419,472 B2 | 9/2008 | Hibner et al. |
| 7,442,187 B2 | 10/2008 | Khayal et al. |
| 7,494,473 B2 | 2/2009 | Eggers et al. |
| 7,504,386 B2 | 3/2009 | Pressato et al. |
| 7,556,615 B2 | 7/2009 | Pettis et al. |
| 7,559,952 B2 | 7/2009 | Pinchuck |
| 7,588,547 B2 | 9/2009 | Deem |
| 7,611,495 B1 | 11/2009 | Gianturco |
| 7,651,475 B2 | 1/2010 | Angel |
| 7,662,110 B2 | 2/2010 | Flaherty |
| 7,664,545 B2 | 2/2010 | Westersten et al. |
| 7,666,339 B2 | 2/2010 | Chaouk et al. |
| D615,192 S | 5/2010 | Mudd et al. |
| 7,722,582 B2 | 5/2010 | Lina et al. |
| 7,762,983 B2 | 7/2010 | Arnissolle |
| 7,850,656 B2 | 12/2010 | McKay et al. |
| 7,850,683 B2 | 12/2010 | Elkins |
| 7,878,981 B2 | 2/2011 | Strother et al. |
| 7,896,837 B2 | 3/2011 | Wilkinson et al. |
| D637,287 S | 5/2011 | Mudd et al. |
| 7,998,170 B2 | 8/2011 | Cunningham |
| 8,012,139 B2 | 9/2011 | McKay et al. |
| 8,029,460 B2 | 10/2011 | Rush et al. |
| 8,066,629 B2 | 11/2011 | Dlugos |
| 8,083,722 B2 | 12/2011 | McKay et al. |
| 8,088,108 B2 | 1/2012 | Kraft |
| 8,157,830 B2 * | 4/2012 | Wenchell ......... A61B 17/07207 606/186 |
| 8,172,815 B2 | 5/2012 | Down et al. |
| 8,216,190 B2 | 7/2012 | Gartstein |
| 8,236,021 B2 | 8/2012 | Kluge |
| 8,291,768 B2 | 10/2012 | Spiegel |
| 8,303,518 B2 | 11/2012 | Aceti |
| 8,303,545 B2 | 11/2012 | Schraga |
| 8,343,132 B2 | 1/2013 | Heneveld et al. |
| 8,349,554 B2 | 1/2013 | Bahrami et al. |
| 8,353,871 B2 | 1/2013 | Zimmerman |
| 8,366,643 B2 | 2/2013 | Deem |
| 8,394,118 B2 | 3/2013 | Jones et al. |
| 8,409,147 B2 | 4/2013 | Kraft |
| 8,409,185 B2 | 4/2013 | Burger |
| 8,480,630 B2 | 7/2013 | Mudd et al. |
| 8,535,278 B2 | 9/2013 | Mudd et al. |
| 8,562,571 B2 | 10/2013 | Mudd et al. |
| 8,603,028 B2 | 12/2013 | Mudd et al. |
| 8,632,501 B2 | 1/2014 | Kraft |
| 8,636,797 B2 | 1/2014 | Chitre et al. |
| 8,657,786 B2 | 2/2014 | Bahrami et al. |
| 8,668,675 B2 | 3/2014 | Chase |
| 8,708,965 B2 | 4/2014 | Boyden |
| 8,712,815 B1 | 4/2014 | Nichols et al. |
| 8,821,446 B2 | 9/2014 | Trautman |
| 8,900,181 B2 | 12/2014 | Knowlton |
| 8,900,186 B2 | 12/2014 | Pettis et al. |
| 8,945,060 B2 | 2/2015 | Bunch |
| 9,017,289 B2 | 4/2015 | Backes |
| 9,017,318 B2 | 4/2015 | Fourkas |
| 9,039,688 B2 | 5/2015 | Palmer, III |
| 9,066,712 B2 | 6/2015 | Fourkas |
| 9,072,498 B2 | 7/2015 | Elkins |
| 9,101,346 B2 | 8/2015 | Burger |
| 9,113,855 B2 | 8/2015 | Burger |
| 9,149,331 B2 | 10/2015 | Deem |
| 9,155,584 B2 | 10/2015 | Fourkas |
| 9,180,273 B2 | 11/2015 | Konstantino |
| 9,214,030 B2 | 12/2015 | Sole et al. |
| 9,227,023 B2 | 1/2016 | Kraft |
| 9,241,753 B2 | 1/2016 | Fourkas |
| 9,254,162 B2 | 2/2016 | Burger |
| 9,289,605 B2 | 3/2016 | Choi |
| 9,314,568 B2 | 4/2016 | Gurtner et al. |
| 9,468,748 B2 | 10/2016 | Bang |
| 2001/0008937 A1 | 7/2001 | Callegaro et al. |
| 2002/0010433 A1 | 1/2002 | Johnson |
| 2002/0026039 A1 | 2/2002 | Bellini et al. |
| 2002/0065483 A1 | 5/2002 | Leon |
| 2002/0133114 A1 | 9/2002 | Itoh |
| 2002/0151843 A1 | 10/2002 | Correa et al. |
| 2003/0028154 A1 | 2/2003 | Ros |
| 2003/0050602 A1 | 3/2003 | Pettis et al. |
| 2003/0078912 A1 * | 4/2003 | Oliver .................. A61M 31/00 |
| 2003/0144632 A1 | 7/2003 | Hommann et al. |
| 2003/0181863 A1 | 9/2003 | Ackley |
| 2003/0199883 A1 | 10/2003 | Laks |
| 2004/0010224 A1 | 1/2004 | Bodmeier |
| 2004/0015133 A1 | 1/2004 | Karim |
| 2004/0092927 A1 | 5/2004 | Podhajsky et al. |
| 2004/0147883 A1 | 7/2004 | Tsai |
| 2004/0192643 A1 | 9/2004 | Pressato et al. |
| 2004/0220532 A1 | 11/2004 | Caizza |
| 2005/0033362 A1 | 2/2005 | Grafton |
| 2005/0085767 A1 | 4/2005 | Menassa |
| 2005/0131353 A1 | 6/2005 | Mossanen-Shams et al. |
| 2005/0137496 A1 | 7/2005 | Walsh et al. |
| 2005/0177117 A1 | 8/2005 | Crocker et al. |
| 2005/0182446 A1 | 8/2005 | DeSantis |
| 2005/0192544 A1 | 9/2005 | Wolbring et al. |
| 2005/0215956 A1 | 9/2005 | Nerney |
| 2005/0261633 A1 | 11/2005 | Khalaj |
| 2006/0041320 A1 | 2/2006 | Matsuda |
| 2006/0079765 A1 | 4/2006 | Neer |
| 2006/0089594 A1 | 4/2006 | Landau |
| 2006/0150742 A1 | 7/2006 | Esnouf |
| 2007/0038181 A1 | 2/2007 | Melamud |
| 2007/0083155 A1 | 4/2007 | Muller |
| 2007/0085767 A1 | 4/2007 | Jung et al. |
| 2007/0100363 A1 | 5/2007 | Dollar et al. |
| 2007/0167920 A1 | 7/2007 | Hommann |
| 2007/0212385 A1 | 9/2007 | David |
| 2007/0250010 A1 | 10/2007 | Hohlfelder et al. |
| 2007/0270710 A1 | 11/2007 | Frass et al. |
| 2008/0015522 A1 | 1/2008 | Yeshurun |
| 2008/0033347 A1 | 2/2008 | D'Arrigo et al. |
| 2008/0058706 A1 | 3/2008 | Zhang |
| 2008/0058839 A1 | 3/2008 | Nobles |
| 2008/0071385 A1 | 3/2008 | Binette et al. |
| 2008/0097325 A1 | 4/2008 | Tanaka et al. |
| 2008/0108952 A1 | 5/2008 | Horvath et al. |
| 2008/0114305 A1 | 5/2008 | Gerondale |
| 2008/0119797 A1 | 5/2008 | Kim |
| 2008/0119876 A1 | 5/2008 | Price et al. |
| 2008/0161772 A1 | 7/2008 | Nayak |
| 2008/0167674 A1 | 7/2008 | Bodduluri et al. |
| 2008/0188816 A1 | 8/2008 | Shimazaki |
| 2008/0200758 A1 | 8/2008 | Orbay et al. |
| 2008/0281278 A1 | 11/2008 | Williams |
| 2009/0088703 A1 | 4/2009 | Azar |
| 2009/0124996 A1 | 5/2009 | Heneveld et al. |
| 2009/0125050 A1 | 5/2009 | Dixon |
| 2009/0143746 A1 | 6/2009 | Mudd et al. |
| 2009/0187118 A1 | 7/2009 | Kim |

(56) References Cited

U.S. PATENT DOCUMENTS

| | | |
|---|---|---|
| 2009/0234322 A1 | 9/2009 | Fischer |
| 2009/0240200 A1 | 9/2009 | Heneveld et al. |
| 2009/0247953 A1 | 10/2009 | Yeshurun |
| 2009/0259180 A1 | 10/2009 | Choi |
| 2009/0275917 A1 | 11/2009 | Azar |
| 2009/0287161 A1 | 11/2009 | Traub |
| 2009/0299328 A1 | 12/2009 | Mudd et al. |
| 2010/0006095 A1 | 1/2010 | Woodcock |
| 2010/0030152 A1 | 2/2010 | Lee et al. |
| 2010/0069848 A1 | 3/2010 | Alferness |
| 2010/0100114 A1 | 4/2010 | Berger |
| 2010/0121307 A1 | 5/2010 | Lockard |
| 2010/0152675 A1 | 6/2010 | McClintock |
| 2010/0152679 A1 | 6/2010 | Tezel |
| 2010/0179488 A1 | 7/2010 | Spiegel |
| 2010/0256594 A1 | 10/2010 | Kimmell |
| 2010/0256596 A1 | 10/2010 | Chomas |
| 2010/0280488 A1 | 11/2010 | Pruiitt et al. |
| 2010/0282774 A1 | 11/2010 | Greter et al. |
| 2010/0286618 A1 | 11/2010 | Choi |
| 2011/0009808 A1 | 1/2011 | AlGhamdi |
| 2011/0021905 A1 | 1/2011 | Patrick et al. |
| 2011/0028910 A1 | 2/2011 | Weber |
| 2011/0092916 A1 | 4/2011 | Tezel et al. |
| 2011/0137286 A1 | 6/2011 | Mudd et al. |
| 2011/0152926 A1 | 6/2011 | Vetrecin |
| 2011/0160674 A1 | 6/2011 | Holmes et al. |
| 2011/0172645 A1 | 7/2011 | Moga |
| 2011/0190974 A1 | 8/2011 | Holmes et al. |
| 2011/0202014 A1 | 8/2011 | Mutzbauer |
| 2011/0218494 A1 | 9/2011 | Assaf |
| 2011/0218497 A1 | 9/2011 | Assaf |
| 2011/0230839 A1 | 9/2011 | Bahrami et al. |
| 2011/0238038 A1 | 9/2011 | Sefi |
| 2011/0263724 A1 | 10/2011 | Gurtner |
| 2011/0319865 A1 | 12/2011 | Buss |
| 2012/0041374 A1 | 2/2012 | Lee |
| 2012/0089211 A1 | 4/2012 | Curtis |
| 2012/0101475 A1 | 4/2012 | Wilmot |
| 2012/0123194 A1 | 5/2012 | Beckman |
| 2012/0123537 A1 | 5/2012 | Manesis et al. |
| 2012/0141532 A1 | 6/2012 | Blanda et al. |
| 2012/0150266 A1 | 6/2012 | Shalev |
| 2012/0245629 A1 | 9/2012 | Gross et al. |
| 2012/0259322 A1 | 10/2012 | Fourkas |
| 2012/0265064 A1 | 10/2012 | Bahrami et al. |
| 2012/0265171 A1 | 10/2012 | Thorne |
| 2012/0296206 A1 | 11/2012 | Bahrami et al. |
| 2013/0012865 A1 | 1/2013 | Sallberg et al. |
| 2013/0018325 A1 | 1/2013 | Schiller et al. |
| 2013/0041346 A1 | 2/2013 | Alon |
| 2013/0096531 A1 | 4/2013 | Estepa et al. |
| 2013/0122068 A1 | 5/2013 | Fermanian et al. |
| 2013/0131632 A1 | 5/2013 | Mudd et al. |
| 2013/0131633 A1 | 5/2013 | Mudd et al. |
| 2013/0150826 A1 | 6/2013 | Almohizea |
| 2013/0184648 A1 | 7/2013 | Inou et al. |
| 2013/0184696 A1 | 7/2013 | Fourkas |
| 2013/0197446 A1 | 8/2013 | Gustafsson |
| 2013/0197449 A1 | 8/2013 | Franklin et al. |
| 2013/0211374 A1 | 8/2013 | Hetherington |
| 2013/0253289 A1 | 9/2013 | Hadvary |
| 2013/0274655 A1 | 10/2013 | Jennings |
| 2013/0274670 A1 | 10/2013 | Mudd et al. |
| 2013/0280755 A1 | 10/2013 | Hubert |
| 2013/0310763 A1 | 11/2013 | Mudd et al. |
| 2014/0012227 A1 | 1/2014 | Sigg et al. |
| 2014/0018770 A1 | 1/2014 | Sutkin |
| 2014/0018835 A1 | 1/2014 | Scherkowski |
| 2014/0066845 A1 | 3/2014 | Mudd et al. |
| 2014/0088502 A1 | 3/2014 | Matheny et al. |
| 2014/0088553 A1 | 3/2014 | Hetherington |
| 2014/0114279 A1 | 4/2014 | Klinghoffer |
| 2014/0121587 A1 | 5/2014 | Sallberg et al. |
| 2014/0128685 A1 | 5/2014 | Na |
| 2014/0128810 A1 | 5/2014 | Ozawa et al. |
| 2014/0162901 A1 | 6/2014 | Bahrami et al. |
| 2014/0170299 A1 | 6/2014 | Gill |
| 2014/0228950 A1 | 8/2014 | Whitcup et al. |
| 2014/0228971 A1 | 8/2014 | Kim |
| 2014/0249504 A1 | 9/2014 | Franklin et al. |
| 2014/0257190 A1 | 9/2014 | Yue et al. |
| 2014/0309590 A1 | 10/2014 | Bahrami et al. |
| 2014/0343481 A1 | 11/2014 | Ignon |
| 2014/0350514 A1 | 11/2014 | Levin |
| 2014/0350516 A1 | 11/2014 | Schwab |
| 2014/0350517 A1 | 11/2014 | Dominguez |
| 2014/0350518 A1 | 11/2014 | Franklin et al. |
| 2014/0350536 A1 | 11/2014 | Allison |
| 2015/0025459 A1 | 1/2015 | Kimmel |
| 2015/0025563 A1 | 1/2015 | Mosharrafa et al. |
| 2015/0119875 A1 | 4/2015 | Fischell et al. |
| 2015/0126929 A1 | 5/2015 | Franklin et al. |
| 2015/0141956 A1 | 5/2015 | Hoffman et al. |
| 2015/0157809 A1 | 6/2015 | Park et al. |
| 2015/0209265 A1 | 7/2015 | Horne |
| 2015/0343147 A1 | 12/2015 | Franklin et al. |
| 2016/0007990 A1 | 1/2016 | Solish et al. |
| 2016/0058488 A1 | 3/2016 | Fourkas |
| 2016/0095984 A1 | 4/2016 | Franklin et al. |
| 2016/0114144 A1 | 4/2016 | Sumida |
| 2016/0144125 A1 | 5/2016 | Franklin |
| 2016/0207253 A9 | 7/2016 | Down et al. |
| 2016/0213854 A1 | 7/2016 | Schwab et al. |
| 2016/0263358 A1 | 9/2016 | Unger |
| 2016/0303314 A1 | 10/2016 | Momose |
| 2017/0080154 A1 | 3/2017 | Mudd et al. |
| 2017/0290987 A1 | 10/2017 | Mandaroux et al. |

FOREIGN PATENT DOCUMENTS

| | | |
|---|---|---|
| CN | 2535071 | 2/2003 |
| CN | 200960353 | 10/2007 |
| EP | 0362484 | 4/1990 |
| EP | 0205915 | 7/1990 |
| EP | 0167662 | 12/1990 |
| EP | 0648474 | 4/1995 |
| EP | 0809968 | 12/1997 |
| EP | 1051988 | 11/2000 |
| EP | 1486218 | 12/2004 |
| EP | 1395320 | 6/2006 |
| EP | 1859827 | 11/2007 |
| EP | 1923086 | 5/2008 |
| EP | 2189173 | 5/2010 |
| EP | 2335755 | 6/2011 |
| EP | 2422832 | 2/2012 |
| EP | 2103262 | 2/2013 |
| EP | 2184016 | 4/2013 |
| EP | 2671516 | 12/2013 |
| FR | 53011 | 9/1945 |
| FR | 2622457 | 5/1989 |
| FR | 2857654 | 1/2005 |
| GB | 2336783 | 5/2003 |
| IN | 209387 | 9/2007 |
| KR | 20120007473 | 1/2012 |
| KR | 101246570 | 3/2013 |
| KR | 20130036921 | 4/2013 |
| KR | 20130130436 | 12/2013 |
| KR | 20130132196 | 12/2013 |
| KR | 20140029007 | 3/2014 |
| RU | 2286803 | 11/2006 |
| WO | WO 90/001349 | 2/1990 |
| WO | WO 92/013579 | 8/1992 |
| WO | WO 94/012228 | 6/1994 |
| WO | WO 96/025965 | 8/1996 |
| WO | WO 97/028840 | 8/1997 |
| WO | WO 99/048601 | 9/1999 |
| WO | WO 01/00190 | 1/2001 |
| WO | WO 02/055135 | 7/2002 |
| WO | WO 2004/022603 | 3/2004 |
| WO | WO 2005/095225 | 10/2005 |
| WO | WO 2006/065837 | 6/2006 |
| WO | WO 2008/086479 | 8/2006 |
| WO | WO 2006/118804 | 11/2006 |

(56) References Cited

FOREIGN PATENT DOCUMENTS

| | | |
|---|---|---|
| WO | WO 2006/133111 | 12/2006 |
| WO | WO 2007/092929 | 8/2007 |
| WO | WO 2007/140381 | 12/2007 |
| WO | WO-2007/140381 A2 | 12/2007 |
| WO | WO 2008/019265 | 2/2008 |
| WO | WO 2008/053481 | 5/2008 |
| WO | WO 2008/072229 | 6/2008 |
| WO | WO 2008/079824 | 7/2008 |
| WO | WO 2008/148071 | 12/2008 |
| WO | WO 2009/003135 | 12/2008 |
| WO | WO 2009/035680 | 3/2009 |
| WO | WO 2009/091099 | 7/2009 |
| WO | WO 2009/098666 | 8/2009 |
| WO | WO 2009/158145 | 12/2009 |
| WO | WO 2010/028025 | 3/2010 |
| WO | WO 2011/016785 | 2/2011 |
| WO | WO 2011/073796 | 6/2011 |
| WO | WO 2011/075731 | 6/2011 |
| WO | WO 2011/109129 | 9/2011 |
| WO | WO 2011/109130 | 9/2011 |
| WO | WO 2012/054301 | 4/2012 |
| WO | WO 2012/054311 | 4/2012 |
| WO | WO 2012/127856 | 9/2012 |
| WO | WO 2012/172424 | 12/2012 |
| WO | WO 2013/005881 | 1/2013 |
| WO | WO 2013/054165 | 4/2013 |
| WO | WO 2013/055832 | 4/2013 |
| WO | WO 2013/082112 | 6/2013 |
| WO | WO 2013/106857 | 8/2013 |
| WO | WO 2014/026044 | 2/2014 |
| WO | WO 2014/034032 | 3/2014 |
| WO | WO 2012/174464 | 5/2014 |
| WO | WO 2014/064536 | 5/2014 |
| WO | WO 2014/189161 | 11/2014 |
| WO | WO 2015/007243 | 1/2015 |
| WO | WO 2015/020982 | 2/2015 |
| WO | WO 2013/065235 | 4/2015 |
| WO | WO 2015/064031 | 5/2015 |
| WO | WO 2015/105269 | 7/2015 |
| WO | WO 2015/127339 | 8/2015 |
| WO | WO 2015/149031 | 10/2015 |
| WO | WO 2016/008845 | 1/2016 |
| WO | WO 2016/022865 | 2/2016 |
| WO | WO 2016/033584 | 3/2016 |
| WO | WO 2016/033586 | 3/2016 |

OTHER PUBLICATIONS

Davidenko et al., "Collagen-hyaluronic acid scaffolds for adipose tissue engineering", ACTA Biomaterialia, vol. 6, No. 10, Oct. 1, 2010, pp. 3957-3968.
Galderma, "New Restylane Skinboosters SmartClick delivery system wins prestigious Red Dot design award," Jul. 4, 2014, retrieved from http://www.galderma.com/News/articleType/ArticleView/articleId/64/New-Restylane-Skinboosters-SmartClick-delivery-system-wins-prestigious-Red-Dot-design-award.
Galderma, "Restylane Smart Click System Injection Device," Mar. 2015, retrieved from http://www.red-dot-21.com/products/restylane-smart-click-system-injection-device-22169.
Hamza et al., "A new external filling device in tissue expansion," Plastic and Reconstructive Surgery, Mar. 1998, vol. 101, No. 3, pp. 813-815.
Indian Patent Application No. 190/CHE/2002, filed Mar. 20, 2002, entitled A Subcutaneous Tissue Expander, 5 pages.
Indian Patent Application No. IN2012KO01267 for Tissue Expander, February 8, 2017, 7 pages.
International Search Report from PCT/US2016/021838, dated May 17, 2016, 3 pages.
International Search Report and Written Opinion from PCT/US2009/045831, dated Feb. 24, 2010, 14 pages.
International Search Report and Written Opinion from PCT/US2014/039265, dated Nov. 18, 2014, 18 pages.
International Search Report and Written Opinion from PCT/US2014/039266, dated Aug. 26, 2014, 13 pages.
Park et al., "Biological characterization of EDC-crosslinked collagen-hyaluronic acid matrix in dermal tissue restoration", Biomaterials, Elsevier Science Publishers BV, vol. 24, No. 9, Apr. 1, 2003, pp. 1631-1641.
Prime Journal, "Galderma to launch two new syringes at AMWC 2014," Mar. 2014, 4 pages.
Turtlepin, "The Painless Direct Dermal Injector" Product Information, JM Biotech Co Ltd, 2013, 18 pages.
Wang et al., "In vivo stimulation of de novo collagen production caused by cross-linked hyaluronic acid dermal filler injections in photodamaged human skin.", Archives of Dermatology, American Medical Association, US, vol. 143, No. 2, Feb. 1, 2007, pp. 155-163.

\* cited by examiner

METHODS OF TREATMENT USING A SYRINGE EXTRUSION ACCESSORY

CROSS REFERENCE TO RELATED APPLICATIONS

This application is a continuation of U.S. patent application Ser. No. 15/011,897, filed Feb. 1, 2016, which is a continuation of U.S. patent application Ser. No. 14/284,285, filed May 21, 2014, which claims the benefit of U.S. Provisional Patent App. No. 61/826,878, filed May 23, 2013, the entire disclosure of each of which is incorporated herein by this specific reference.

TECHNICAL FIELD

The present invention generally relates to methods of treatments using medical injection device accessories, and more specifically relates to methods of treatment using a medical syringe extrusion accessory designed to facilitate aliquot dosing.

BACKGROUND

The ability to accurately assess correct injection dosage is most commonly associated with visual cues. For example, volumetric marks already come printed or etched on the side of conventional syringe bodies, and this remains the most common form of measurement. A practitioner injects a certain amount of a substance, such as a drug, by verifying fluid level using these volumetric marks.

Even more generally, a physician can intake an amount of a drug to be injected into the syringe using the volumetric marks. Then, a practitioner can simply expel the entire volume into a patient in a single plunger run. Such a full expulsion of drug removed the need to only inject a portion of a drug in a syringe. Thus, for pharmaceutical drugs, the benefits of injecting the correct dosage should not require explanation.

However, in applications using sensitive drugs such as botulinum toxin or aesthetic soft tissue fillers, for example, hyaluronic acid-based dermal fillers such as Juvederm® XC, manufactured by Allergan, Inc., dose indication provides the practitioner with additional control over precise facial sculpting.

Additionally, with applications like botulinum toxin, injection of multiple small, precise doses of toxin may be advantageous over injection of a large bolus of the material.

Further, with fat grafting, injection of multiple small, precise doses of fat cell-containing material may be advantageous over injection of a single large bolus of the material. Smaller bolus injection increases retention of the injected material, possibly by providing greater vascularization of the material throughout the fat cells and improving survivability thereof. Injection of a large bolus is less likely to be retained long term as the injected fat cells are may be more prone to die, due to lack of vascularization, for example.

Many of these injectable materials, for example, dermal fillers and fat grafting materials, are not easily extruded through standard syringes and accompanying cannula. These materials tend to provide significant resistance to be pushed through a narrow cannula. The problem is even more exacerbated by the fact that these materials are often used for detailed precision work in facial contouring and body sculpting.

Injection devices, both manual and motorized, have been specifically developed, or at least proposed, to address these issues. Interestingly, many physicians prefer the use of manual conventional syringe injectors over electronically controlled, motorized devices. For at least this reason, there remains a need for devices (e.g., simple devices) that can be attached to a standard syringe and which provide better control over small aliquot dosing of relatively difficult to inject materials, for example, dermal fillers, fat grafting materials and the like.

The description provided in the background section should not be assumed to be prior art merely because it is mentioned in or associated with the background section. The background section may include information that describes one or more aspects of the subject technology.

SUMMARY

Disclosed herein are mechanical dosing accessories and/or syringe extrusion accessories configured to be attached to, coupled to, or incorporated into standard syringes. The dosing accessories are configured to provide improved mechanical advantage or leverage and dosing capability, relative to a conventional syringe alone. In some embodiments, the accessories described can be used in conjunction with conventional syringes for injection of substances. The substances or products can be highly viscous such as, but not limited to, dermal fillers or fat grafting materials.

Various embodiments of the present disclosure are directed to methods of treatment using syringe extrusion accessories. The method may include providing a syringe having a medicinal fluid therein for administering to a patient, and coupling an attachment portion of an extrusion accessory having a handle and a pawl to a flange portion of the syringe. The handle may be hingedly coupled to the attachment portion. The pawl may have first and second ends, and be hingedly and rotatably coupled relative to the handle at a first position at the first end and at a second position between the first and second ends. The method may further include applying a force to translate the handle in a direction that is substantially perpendicular relative to a longitudinal axis of the syringe to cause axial movement of the second end of the pawl. The second end of the pawl may be engaged with a plunger of the syringe and axial movement of the second end of the pawl drives the plunger forward to extrude the medicinal fluid from the syringe.

In some embodiments, a method of dispensing a medicinal fluid in a predetermined dosage for treatment of a patient may include applying a force to translate a handle of an extrusion accessory, coupled to a syringe, in a direction that is substantially perpendicular relative to a longitudinal axis of the syringe. The extrusion accessory may include a pawl having first and second ends and may be hingedly and rotatably coupled relative to the handle at the first end of the pawl and at a position between the first and second ends. The application of force to the handle may move the second end of the pawl for engaging with and pushing a plunger of the syringe axially for extruding the medicinal fluid from the syringe.

It is to be understood that both the foregoing general description and the following detailed description are exemplary and explanatory and are intended to provide further explanation of the subject technology as claimed. It is also to be understood that other aspects may be utilized, and changes may be made without departing from the scope of the subject technology.

BRIEF DESCRIPTION OF THE DRAWINGS

Embodiments of the present description are illustrated by way of example, and not by way of limitation, in the figures of the accompanying drawings and in which like reference numerals refer to similar elements, wherein.

DETAILED DESCRIPTION

Generally described are syringe accessories such as, but not limited to mechanical dosing accessories and/or syringe extrusion accessories that can be attached to a conventional syringe and provide a transfer of perpendicular force to axial force for injection. In other embodiments, an accessory as described herein can be permanently mounted to a syringe using, for example, glue or adhesive. In still other embodiments, a syringe including an accessory as described herein can be produced as a single integrated device.

Figure 1:
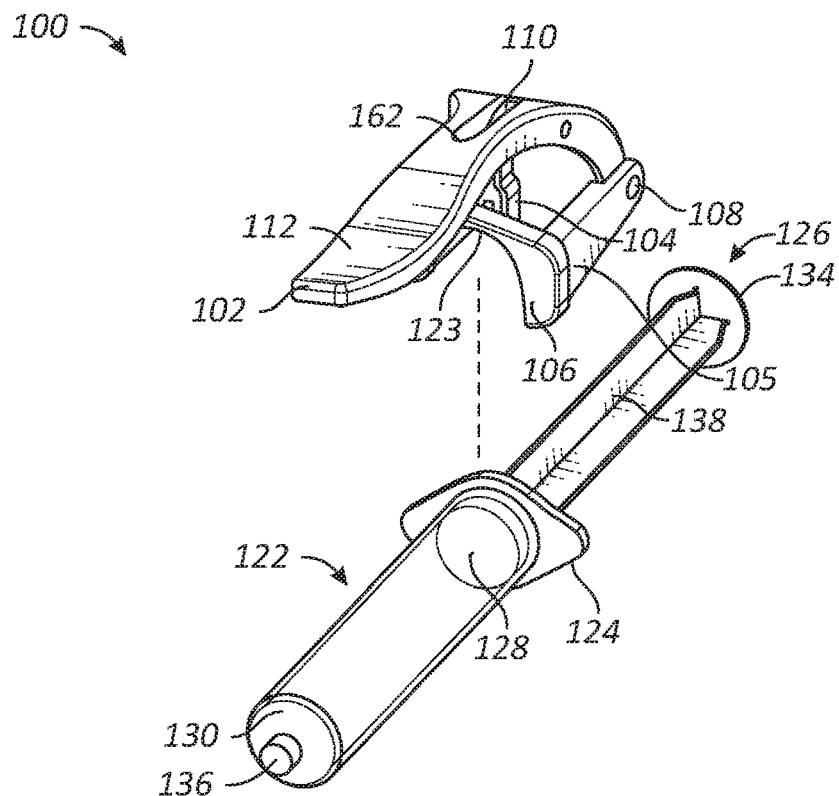
FIG. 1 illustrates a perspective view of a syringe and a syringe extrusion accessory as described herein.
Figure 2:
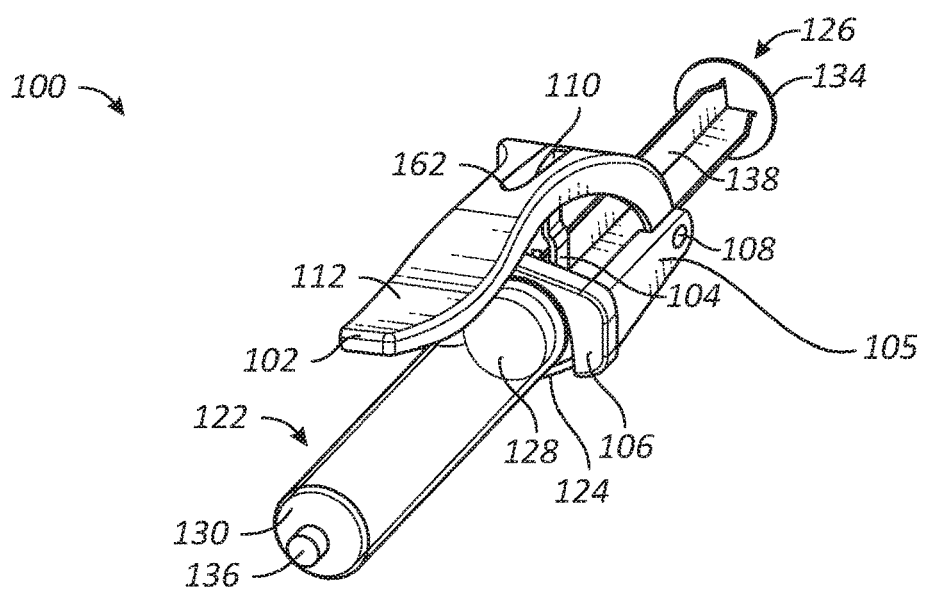
FIG. 2 illustrates a perspective view of a syringe with an extrusion accessory as illustrated in FIG. 1 attached thereto.

As illustrated in FIGS. 1-2, an accessory 100 as described herein can generally include handle 102, pawl 104, attachment portion 106, a first hinge 108 and a second hinge 110.

Handle 102 can optionally include a finger indentation region 112 wherein a user can apply a substantially perpendicular force to a depressed portion thereby focusing the force to a substantially predetermined point on handle 102. Handle 102 can be configured to accept a substantially perpendicular input force and transfer that force to pawl 104.

Pawl 104 is operably attached to handle 102 through second hinge 110. Pawl 104 can have a generally sinusoidal shape having a first end 114 terminating at second hinge 110 and second end 116 terminating at one or more claws 118. First end 114 can be curved toward the proximal end 130 of syringe 122 when fully extended in use thereby achieving the translation of force provided by the accessories. Second end 116 can be curved toward the distal end of syringe 122 when fully extended in use.

Pawl 104 can be operably configured to move one or more claws 118 in generally axial direction 120. Pawl 104 can include one, two, three, four, five, six, seven, eight, nine, ten, eleven, twelve, 13, 14, 15, 16, 17, 18, 19, 20, or more claws. As such, based on substantially perpendicular movement of handle 102, claws 118 can in turn be moved in axial direction 120 through second hinge 110.

Further, handle 102 is operably connected to attachment portion 106 through first hinge 108. Attachment portion 106 is configured to allow attachment of accessory 100 to syringe 122. In one embodiment, accessory 100 can be attached to syringe 122 at flange 124. Attachment portion 106 can be shaped to at least partially engage flange 124. In some embodiments, attachment portion 106 can engage between about 20% and about 80%, between about 30% and about 60%, between about 40% and about 60%, between about 50% and about 70%, or between about 60% and about 80% of flange 124. Attachment portion 106 can engage with flange 124 using a friction fit, a locking fit where attachment portion 106 includes locking features that snap and lock once the two parts are engaged, or a glue engagement wherein attachment portion 106 and flange 124 are glued together.

Substantially perpendicular force applied to handle 102 can be translated to force in axial direction 120. Claws 118 can engage plunger 126 and provide an axial force thereby driving plunger head 128 toward proximal end 130 of syringe 122.

Substantially perpendicular force can be applied at an angle 132 which is substantially perpendicular to syringe 122. Angle 132 can be about 1 degree, about 5 degrees, about 10 degrees, about 15 degrees, about 20 degrees, about 25 degrees, less than about 5 degrees, less than about 10 degrees, less than about 15 degrees, between about 1 degree and about 10 degrees, between about 1 degree and about 20 degrees, or between about 5 degrees and about 25 degrees.

This substantially perpendicular force can replace axial forces that typically must be applied to plunger finger surface 134. With highly viscous materials such as dermal fillers and fat grafting substances, substantial axial forces must be applied in order to extrude these materials from a needle or other delivery device attached to luer tip 136 or other attachment interface. This need to apply a substantial force to plunger finger surface 134 requires a user to balance applying axial forces to the syringe with resisting axial forces of a needle into the tissue.

In some embodiments, luer tip 136 or other attachment interface can be configured to attach to a cannula or needle which is suitable for introducing contents of syringe 122 into a target region of a patient for tissue bulking, augmentation or reconstructive purposes.

In other embodiments, luer tip 136 or other attachment interface can be configured to attach to flexible tubing or a conduit which is suitable for introducing contents of syringe 122 into a target region of a patient for tissue bulking, augmentation or reconstructive purposes. Such embodiments may allow for enhanced flexibility and ergonomic grip of a cannula or a needle.

A cannula or a needle as used herein can be a 10, 12, 14, 16, 18, 20, 22 up to 33 gauge, or other gauges. In some embodiments, the needle gauge may be one suitable for fat grafting or dermal filler purposes. In one embodiment, the needle gauge is between 10 and 33. The length of a needle can be any appropriate length known in the art. In one embodiment, the needle length is about 1/16 inch to about 3 inches, more generally about 1/16 inch to about 2 inches. A cannula or a needle may be blunt or sharp tipped.

Pawl 104 can be configured to engage with a given plunger style. Plungers can have various shapes for stem portion 138. For example, as illustrated in the Figures, stem 138 includes vertical appendage 140 and horizontal appendage 142. Thus, in one embodiment, pawl 104 can be split at second end 116 thereby straddling vertical appendage 140 without touching it and engaging both sides of horizontal appendage 142.

In other embodiments, stem portion 138 may have a cylindrical shape or circular cross-section. In such embodiments, pawl 104 can have a single second end 116 or an un-split second end. This single second end 116 can engage stem portion 138 along its cylindrical surface.

Various other stem shapes can be used and skilled artisans will understand how to modify pawl 104 to engage these types of plungers and translate substantially perpendicular force to axial force on the plunger.

Figure 4:
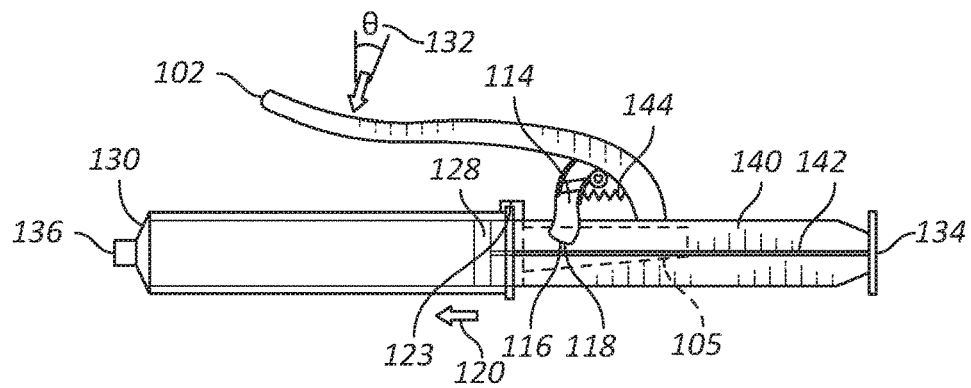
FIG. 4 illustrates a second step in using an extrusion accessory wherein a substantially perpendicular force is applied to the accessory's handle thereby applying an axial force to the syringe's plunger.
Figure 5:
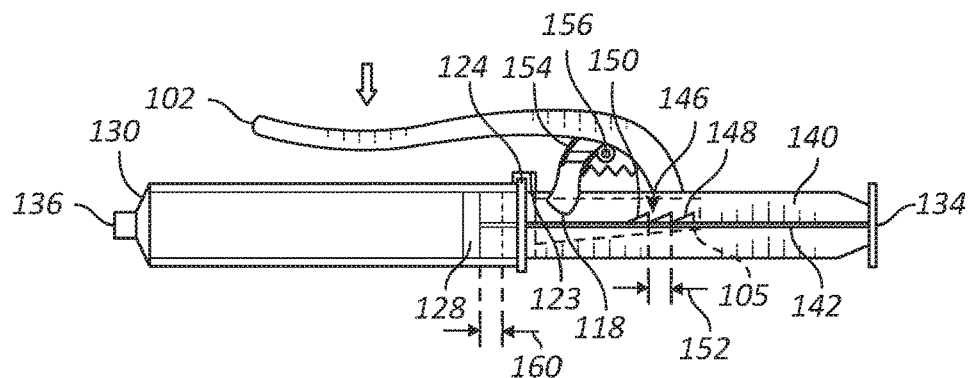
FIG. 5 illustrates a third step in using an extrusion accessory wherein a substantially perpendicular force is applied to the accessory's handle until the pawl can no longer extend from the handle indicating the end of an injection sequence.
Figure 6:
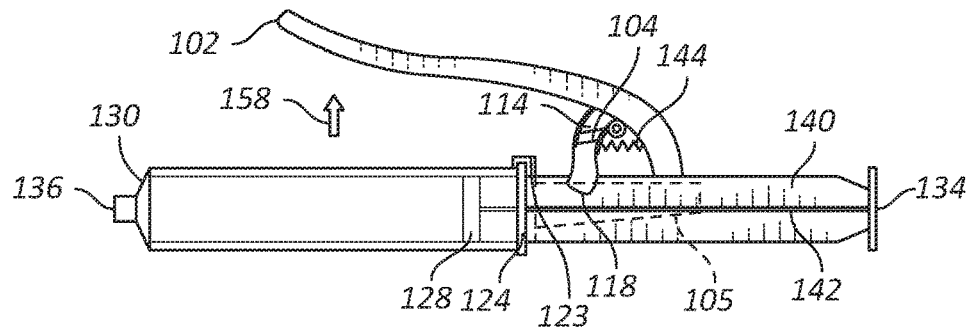
FIG. 6 illustrates a reset of the extrusion accessory to extrude a further amount of substance from the syringe.

In some embodiments, spring 144 can be provided to couple pawl 104 to handle 102 as illustrated in FIGS. 3-6. Spring 144 can provide a resistive or compressive force as handle 102 is depressed. When handle 102 is disengaged, thereby disengaging pawl 104 from plunger 126, spring 144 can compress thereby pulling pawl 104 toward handle 102 as illustrated in FIG. 6 thereby "re-setting" the device.

In some embodiments, tracks can be provided on plunger 126 for claws 118 to engage. For example, as illustrated in FIG. 5, in some embodiments, tracks 146 can be located on vertical appendage 140 and/or horizontal appendage 142.

An exemplary track system can be configured to allow claws 118 to engage in one or more valleys 150 between adjacent teeth 148. In some embodiments, teeth 148 can have a generally rounded or oval surface preventing claw leverage onto the plunger. Each valley 150 between adjacent teeth 148 can be spaced a predetermined distance 152 from the next valley 150.

In other embodiments, teeth 148 can be configured to have a generally wave-like shape. When a claw is engaged in a valley 150 with a long front surface and a short back surface, claws 118 can provide force against the short wall of teeth 148. In some embodiments, an accessory 100 can include a plunger that has tracks that can be used with accessory 100. When a plunger is provided, the syringe plunger can be replaced with the provided plunger.

In other embodiments, a track or set of tracks can be provided to be attached to a plunger. In these embodiments, tracks can be glued to the plunger stem prior to use. In other embodiments, tracks can be snapped around a plunger stem.

Each valley 150 between adjacent ratcheting teeth 148 can be spaced 152 from the next valley. Each space 152 can be equivalent to a predetermined amount of substance ejected from the syringe. This is the case because movement of track 146 a particular distance moves plunger 126 which eventually moves plunger head 128 the same axial distance.

Accessory 100 can be formed of metal, a polymer, or a combination thereof. In some embodiments, accessory 100 can include materials such as, but not limited to, rigid thermoplastics, thermoplastic elastomers, silicones, glass, metals, composite materials, carbons fillers, or any combination thereof.

The accessories described herein can allow an operator to easily inject viscous substances or materials through any size needle known in the art by applying substantially perpendicular force to the handle. The accessories make the syringe easy to hold, manipulate and operate with one hand, and in some cases adjust easily with the operator's opposing hand. The accessories can allow the operator to precisely control the injection speed (or extrusion rate) being injected. The accessories can also allow an operator to still see the graduation or volume markings on the syringe body thereby allowing an operator to visualize initial volume, volume injected and remaining volume of substance in the syringe.

Further, the accessories described herein can have an ergonomic shape that allows the operator to hold and inject from the syringe easily. Unlike traditional syringes which do not conform to any ergonomic aspect of the hand, the present devices can have at least one ergonomic design shaped into the accessories such as finger indentation region 112. Additionally, the present accessories can accommodate operator hands of different sizes. Hand size accommodation can be accomplished by different device sizes, position-adjustable device handles or interchangeable device handles. For example, interchangeable handles can come in various pre-determined sizes or can be personalized for a particular user.

Figure 3:
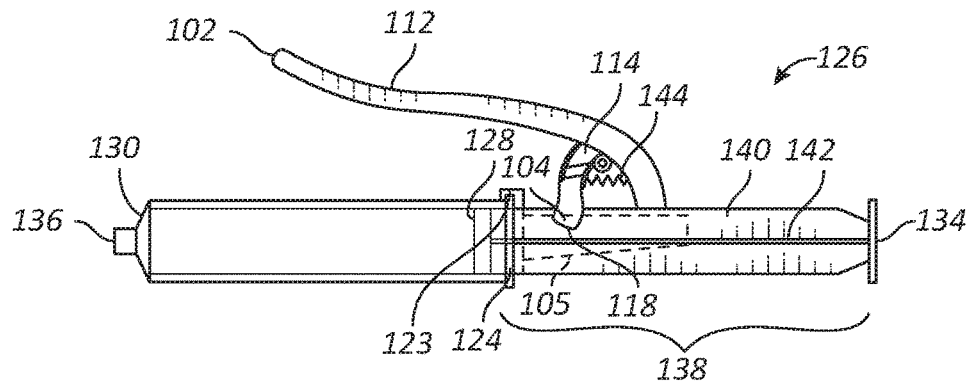
FIG. 3 illustrates a first step in using an extrusion accessory wherein the accessory is added to the syringe and prepared for use.

Methods of using the accessories described are also contemplated. For example, in some embodiments, an accessory is provided and attached to a syringe preferably at the syringe flange 124 as illustrated in FIG. 3. Spring 144 can be configured to rest handle 102 at a predetermined angle 132 relative to syringe 122 with claws 118 resting against plunger stem 138.

Then, as illustrated in FIG. 4, force is applied to handle 102 substantially perpendicular to syringe 122, thereby driving axial force to plunger 126 as translated by pawl 104.

When a particular spring force has been exhausted or a stop 154 on the underside of handle 102 has been reached, plunger 126 will not be moved axially any further as illustrated in FIG. 5. At this point, a full extension of accessory 100 has been achieved.

In other embodiments, full extension of accessory 100 can be achieved when pawl 104 abuts handle 102 at leading edge 162.

The force applied to move from predetermined angle 132 illustrated in FIG. 3 to the full extension of accessory 100 in FIG. 5 can translate into a predetermined dose of extruded content. For example, the force can translate into about 0.1 mL, about 0.5 mL, about 1 mL, about 2 mL, about 3 mL, about 4 mL, about 5 mL, about 10 mL, about 15 mL, about 20 mL, between about 0.1 mL and about 10 mL, between about 1 mL and about 10 mL, or between about 0.5 mL and about 5 mL. In other embodiments, a second stop 156 can be supplied such that pawl 104 can only travel between second stop 156 and stop 154. This distance of pawl 104 travel can be equivalent to an extruded amount from syringe 122.

For example, in some embodiments, predetermined distance 152 can define a dosage of substance because predetermined distance 152 can cause axial movement of plunger head 128 a second pre-determined distance 160. This second pre-determined distance 160 in turn represents a particular volume of substance extruded from syringe 122.

In other embodiments, the use of accessory 100 may not deliver a predetermined amount of substance or material but rather the amount delivered may still require use of visual marks on syringe 122.

In any circumstance, whether pre-determined or manual delivery amounts, once full extension of accessory 100 is achieved, claws 118 can be disengaged from plunger 126 by pulling handle 102 upward and away from syringe 122 as illustrated in FIG. 6. This disengagement can "re-set" the accessory to reengage the plunger 126 and deliver a subsequent dose of substance or material.

In some embodiments, when spring 144 is used, the upward force 158 needed to disengage claws 118 from plunger 126 can be reduced. Also, using spring 144 can pull pawl 104 toward handle 102 thereby "re-setting" accessory 100 for subsequent delivery.

Kits including an accessory as described herein are also contemplated. A kit can include an accessory that is configured to be attached to a syringe and instructions for use. In other embodiments, a kit can include an accessory, a syringe and instructions for use. In still other embodiments, a kit can include an accessory, a syringe filled with an injectable substance or a separate vial including the substance, and instructions for use. In other embodiments, a kit can include a syringe including an integrated accessory. In other embodiments, a kit can include a syringe including an integrated accessory and an injectable substance within the syringe or in a vial in the kit.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of treatment comprising:
providing a conventional syringe having a medicinal fluid therein for administering to a patient, the conventional syringe comprising a cylindrical body, a flange portion extending radially outwardly from the cylindrical body at a distal portion thereof, and a plunger reciprocally disposed within the cylindrical body;
coupling an attachment portion of an extrusion accessory to the flange portion of the syringe, the extrusion accessory having a handle hingedly coupled to the attachment portion and a pawl having first and second ends, the pawl being hingedly and rotatably coupled relative to the handle at a first position at the first end and via a pawl-coupling, at a second position between the first and second ends;
applying a force to translate the handle in a direction that is substantially perpendicular relative to a longitudinal axis of the syringe to cause axial movement of the second end of the pawl, wherein the second end of the pawl is engaged with the plunger of the syringe and axial movement of the second end of the pawl drives the plunger forward to extrude the medicinal fluid from the cylindrical body of the syringe; and
permitting the pawl and the handle to be repositioned by foreshortening of the pawl-coupling between the pawl and the handle such that the pawl is pulled towards the handle.

2. The method of claim 1, wherein the pawl includes a claw positioned at the second end thereof and the plunger includes a stem portion, and the applying comprises engaging the claw with the stem portion.

3. The method of claim 2, wherein the stem portion comprises a vertical appendage and a horizontal appendage, and wherein during the applying, the claw engages the vertical appendage or the horizontal appendage to provide an axial force to drive the plunger towards a proximal end of the syringe.

4. The method of claim 3, wherein the pawl includes a split at the second end thereof, wherein during the applying, opposing sides of the horizontal appendage are engaged with corresponding opposing sides of the split of the pawl while straddling without contacting the vertical appendage.

5. The method of claim 4, wherein at least one of the horizontal appendage or the vertical appendage comprise a set of tracks including pairs of adjacent teeth each interposed by a valley therebetween, the valleys each being spaced apart a predetermined distance, and wherein the applying comprises translating the handle to move the pawl along the predetermined distance to extrude a predetermined dosage of the medicinal fluid from the syringe.

6. The method of claim 2, wherein the stem portion comprises a vertical appendage and a horizontal appendage, and the applying comprises engaging the claw with the horizontal appendage to provide an axial force to drive the plunger towards a proximal end of the syringe.

7. The method of claim 1, wherein the pawl is coupled to the handle through a hinge at the first end, the pawl having a generally sinusoidal shape with the first end terminating at the hinge, and wherein during the applying, the first end curves towards a proximal end of the syringe when the first end is in a fully extended position in use so as to translate the substantially perpendicular force to the axial movement.

8. The method of claim 1, wherein a proximal end of the syringe comprises a luer tip attached to a cannula or a needle, the method further comprising introducing the medicinal fluid from the syringe, through the cannula or the needle, into a target region of a patient for tissue bulking, augmentation or reconstructive purposes.

9. The method of claim 8, wherein the introducing is performed for fat grafting or dermal filler purposes.

10. The method of claim 1, wherein the pawl-coupling couples the pawl to the handle at the second position through a compression spring.

11. The method of claim 1, wherein the applying comprises applying the substantially perpendicular force at an angle of between about 1 degree and about 20 degrees relative to a line normal to the longitudinal axis of the syringe.

12. The method of claim 1, wherein coupling the extrusion accessory to the syringe comprises attaching the attachment portion to the flange portion of the syringe by a snap fit, a friction fit, a glue, an adhesive, or a combination thereof.

13. A method of dispensing a medicinal fluid in a predetermined dosage for treatment of a patient, the method comprising applying a force to translate a handle of an extrusion accessory, coupled to a conventional syringe, in a direction that is substantially perpendicular relative to a longitudinal axis of the syringe, the syringe comprising a cylindrical body in which the medicinal fluid is disposed, a flange portion extending radially outwardly from the cylindrical body at a distal portion thereof, and a plunger reciprocally disposed within the cylindrical body, the extrusion accessory comprising a pawl having first and second ends and being hingedly and rotatably coupled relative to the handle at the first end of the pawl and via a pawl-coupling at a second position between the first and second ends, wherein application of force to the handle moves the second end of the pawl for engaging with and pushing the plunger of the syringe axially for extruding the medicinal fluid from the cylindrical body of the syringe, and wherein releasing the force on the handle permits the pawl and the handle to be repositioned by action of the pawl-coupling between the pawl and the handle such that the pawl is pulled towards the handle.

14. The method of claim 13, wherein the pawl includes a claw positioned at the second end thereof and the plunger includes a stem portion, the engaging the second end of the pawl with the plunger comprising engaging the claw with the stem portion.

15. The method of claim 14, wherein the stem portion comprises a vertical appendage and a horizontal appendage, and wherein the applying comprises engaging the claw with the vertical appendage or the horizontal appendage to provide an axial force to drive the plunger towards a proximal end of the syringe.

16. The method of claim 13, wherein the syringe comprises a luer tip attached to a cannula or needle, and wherein the applying comprises extruding the predetermined dosage of medicinal fluid from the syringe by pushing the plunger to introduce the medicinal fluid through the needle from the syringe and into a target region of a patient for tissue bulking, augmentation or reconstructive purposes.

17. The method of claim 16, wherein the needle has a gauge sized for fat grafting or dermal filler purposes.

18. The method of claim 17, wherein the applying comprises applying the substantially perpendicular force at an angle of between about 1 degree and about 20 degrees relative to a line normal to a longitudinal axis of the syringe.

19. The method of claim 13, wherein the pawl-coupling couples the pawl to the handle at the second position through a compression spring, the method further comprising permitting the pawl and handle to be urged to a reset position via action of the spring-coupling such that the pawl is pulled towards the handle.

20. An extrusion accessory for a conventional syringe, the accessory comprising:
an attachment portion couplable to a flange portion of the conventional syringe; a handle hingedly coupled to the attachment portion; and
a pawl having first and second ends, the pawl being hingedly and rotatably coupled relative to the handle at a first position at the first end and at a second position, via a pawl-coupling, between the first and second ends such that application of force to the handle moves the second end of the pawl for engaging with and pushing plunger of the syringe axially for extruding the medicinal fluid from the cylindrical body of the syringe, and releasing the force on the handle permits the pawl and the handle to be repositioned by action of the pawl-coupling between the pawl and the handle such that the pawl is pulled towards the handle.

* * * * *